United States Patent [19]
Kast et al.

[11] Patent Number: 5,523,462
[45] Date of Patent: Jun. 4, 1996

[54] CYCLOHEXENONE DERIVATIVES

[75] Inventors: Juergen Kast; Thomas Zierke, both of Boehl-Iggelheim; Matthias Bratz, Speyer; Ulf Misslitz, Neustadt; Norbert Meyer, Ladenburg; Andreas Landes; Wilhelm Rademacher, both of Limburgerhof; Karl-Otto Westphalen, Speyer; Helmut Walter, Obrigheim, all of Germany

[73] Assignee: BASF Aktiengesellschaft, Ludwigshafen, Germany

[21] Appl. No.: 211,819

[22] PCT Filed: Sep. 26, 1992

[86] PCT No.: PCT/EP92/02226
§ 371 Date: Apr. 19, 1994
§ 102(e) Date: Apr. 19, 1994

[87] PCT Pub. No.: WO93/08153
PCT Pub. Date: Apr. 29, 1993

[30] Foreign Application Priority Data

Oct. 25, 1991 [DE] Germany .......................... 41 35 265.3

[51] Int. Cl.⁶ .......................... C07C 69/75; A01N 37/06; A01N 37/08
[52] U.S. Cl. .......................... 560/126; 504/313; 504/319; 504/335; 560/125; 564/152
[58] Field of Search .......................... 560/125, 126; 504/319, 313, 335; 564/152

[56] References Cited

U.S. PATENT DOCUMENTS

| | | | |
|---|---|---|---|
| 4,011,256 | 3/1977 | Sawaki et al. | 260/468 J |
| 4,249,937 | 2/1981 | Iwataki et al. | 71/97 |
| 4,584,013 | 4/1986 | Brunner et al. | 71/94 |
| 4,640,706 | 2/1987 | Brunner et al. | 71/94 |
| 4,866,201 | 9/1989 | Motojima et al. | 560/126 |
| 4,954,160 | 9/1990 | Gilkerson et al. | 71/88 |

FOREIGN PATENT DOCUMENTS

| | | |
|---|---|---|
| 1205813 | 6/1986 | Canada . |
| 123001 | 10/1984 | European Pat. Off. . |
| 177450 | 4/1986 | European Pat. Off. . |
| 199658 | 10/1986 | European Pat. Off. . |
| 293817 | 12/1988 | European Pat. Off. . |
| 338525 | 10/1989 | European Pat. Off. . |
| 368227 | 5/1990 | European Pat. Off. . |
| 833488 | 9/1975 | France . |
| 2439104 | 8/1975 | Germany . |
| 2461027 | 11/1975 | Germany . |
| 4014988 | 11/1991 | Germany . |
| 4014987 | 11/1991 | Germany . |
| 4014986 | 11/1991 | Germany . |
| 4014983 | 11/1991 | Germany . |
| 4014984 | 11/1991 | Germany . |

OTHER PUBLICATIONS

Derwent Abstract—J 5 7045–143 (1982).
Derwent Abstract—J5 1013–750 (1976).
Derwent Abstract—J5 7046–943 (1982).
Derwent Abstract—J5 4016 454 (1979).
Derwent Abstract—J5 1131 856 (1976).
The Chemical Structure and Herbicidal Activity . . . Iwataki et al. (1980).

*Primary Examiner*—José G. Dees
*Attorney, Agent, or Firm*—Keil & Weinkauf

[57] ABSTRACT

Cyclohexenone derivatives I

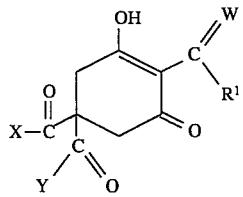

The cyclohexenone derivatives I are suitable as herbicides and for regulating plant growth.

7 Claims, No Drawings

CYCLOHEXENONE DERIVATIVES

This application is a 371 of PCT/EP92/02226, filed Sep. 26, 1992.

The present invention relates to novel cyclohexenone derivatives of the general formula I

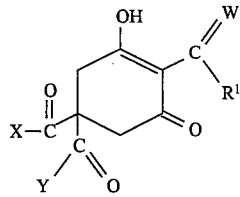

where the variables have the following meaning: $R^1$ is $C_1$–$C_{20}$-alkyl, $C_2$–$C_{20}$-alkenyl, $C_2$–$C_{20}$-alkynyl, $C_3$–$C_6$-cycloalkyl, $C_1$–$C_4$-alkoxy-$C_1$–$C_4$-alkyl, $C_1$–$C_4$-alkylthio-$C_1$–$C_4$-alkyl, phenyl, benzyl or a 5-membered or 6-membered hetaryl group having one or two heteroatoms selected from the group consisting of nitrogen, oxygen and sulfur, where the aromatic and heteroaromatic rings may, if desired, furthermore carry from one to three radicals selected from the group consisting of nitro, cyano, halogen, $C_1$–$C_4$-alkyl, partially or completely halogenated $C_1$–$C_4$-alkyl, $C_1$–$C_4$-alkoxy, $C_1$–$C_4$-alkylsulfinyl and $C_1$–$C_4$-alkylsulfonyl;

W is oxygen, $=$N—$OR^2$ or $=$N—$R^3$, where $R^2$ is $C_1$–$C_6$-alkyl, $C_3$–$C_6$-alkenyl or $C_3$–$C_6$-alkenyl [sic], where these radicals may furthermore carry from one to three of the following substituents selected from the group consisting of halogen, $C_1$–$C_4$-alkyl, $C_1$–$C_4$-alkoxy, phenyl and 5-membered and 6-membered hetaryl having one or two heteroatoms selected from the group consisting of nitrogen, oxygen and sulfur, and the phenyl and hetaryl substituents in turn may furthermore carry from one to three radicals selected from the group consisting of nitro, halogen, $C_1$–$C_4$-alkyl, partially or completely halogenated $C_1$–$C_4$-alkyl, $C_1$–$C_4$-alkoxy and partially or completely halogenated $C_1$–$C_4$-alkoxy;

a 3-membered to 6-membered alkyl chain or a 4-membered to 6-membered alkenyl or alkynyl chain, where one chain member in each case is replaced by oxygen, sulfur or —SO—, —SO2— [sic] or —N($R^8$)— and the chain may furthermore additionally carry from one to three substituents selected from the group consisting of halogen, $C_1$–$C_4$-alkyl, $C_1$–$C_4$-alkoxy, phenyl and 5-membered and 6-membered hetaryl having one or two hetero atoms selected from the group consisting of nitrogen, oxygen and sulfur, and the phenyl and hetaryl substituents may in turn furthermore carry from one to three radicals selected from the group consisting of nitro, halogen, $C_1$–$C_4$-alkyl, partially or completely halogenated $C_1$–$C_4$-alkyl, $C_1$–$C_4$-alkoxy and partially or completely halogenated $C_1$–$C_4$-alkoxy, where $R^8$ is hydrogen, $C_1$–$C_6$-alkyl, $C_1$–$C_6$-alkenyl, $C_1$–$C_6$-alkynyl, $C_1$–C6-alkylcarbonyl [sic] or benzoyl;

$R^3$ is hydrogen, $C_1$–$C_6$-alkyl, hydroxy-$C_1$–$C_4$-alkyl, $C_1$–$C_4$-alkoxy-$C_1$- or $C_2$-alkyl, $C_1$–$C_4$-alkylthio-$C_1$-or $C_2$-alkyl, phenyl or benzyl, where the aromatic rings may furthermore carry from one to three substituents selected from the group consisting of nitro, halogen, $C_1$–$C_4$-alkyl, partially or completely halogenated $C_1$–$C_4$-alkyl and $C_1$–$C_4$-alkoxy;

X and Y are each —$OR^4$ or —$NR^5R^6$, where $R^4$ is hydrogen, $C_1$–$C_6$-alkyl, $C_3$–$C_6$-alkenyl, $C_3$–$C_6$-alkynyl, $C_1$–$C_4$-alkoxy-$C_1$–$C_4$-alkyl or $C_1$–$C_4$-alkyl thio -$C_1$–$C_4$-alkyl, $R^5$ is hydrogen, $C_1$–$C_6$-alkyl, $C_3$–$C_6$-alkenyl, $C_3$–$C_6$-alkynyl, hydroxy-$C_1$–$C_4$-alkyl, $C_1$–$C_4$-alkoxy-$C_1$–$C_4$-alkyl or $C_1$–$C_4$-alkylthio-$C_1$–$C_4$-alkyl and $R^6$ is hydrogen, $C_1$–$C_6$-alkyl, $C_3$–$C_6$-alkenyl, $C_3$–$C_6$-alkynyl, hydroxy-$C_1$–$C_4$-alkyl, $C_1$–$C_4$-alkoxy-$C_1$–$C_4$-alkyl, $C_1$–$C_4$-alkylthio-$C_1$–$C_4$-alkyl or $C_1$–$C_6$alkylcarbonyl or benzoyl which may furthermore carry from one to three substituents selected from the group consisting of nitro, cyano, halogen, $C_1$–$C_4$-alkyl, partially or completely halogenated $C_1$–$C_4$-alkyl, $C_1$–$C_4$-alkoxy and $C_1$–$C_4$alkylthio, or $R^5$ and $R^6$, together with the nitrogen atom to which they are bonded, by form a 5-membered or 6membered heterocyclic structure which may contain an oxygen or sulfur atom or —N($R^7$)— as a ring member, where $R^7$ is hydrogen, $C_1$–$C_6$-alkyl, $C_3$–$C_6$-alkenyl, $C_3$–$C_6$-alkynyl, $C_1$–$C_6$-alkylcarbonyl or benzoyl, and their agriculturally useful salts and esters of $C_1$–$C_{10}$-carboxylic acids and inorganic acids.

The present invention furthermore relates to processes for the preparation of these compounds, their use as herbicides and for regulating plant growth, and herbicidal agents and agents for regulating plant growth which contain the compounds as active ingredients.

The literature discloses herbicidally active cyclohexenone derivatives which carry an oxime ether group in the 2-position (U.S. Pat. No. 4,249,937; CA 1,205,813; Adv. Pest. Science, Part 2, Pergamon Press, Zurich, 1978; E. H. Geissb ühler, Proc. 4th Inern. [sic] Congress of Pesticide Chemistry (IUPAC), 1978, 235; EP-A-0 368 227, DE-A-40 14 983, DE-A-40 14 984, DE-A-40 14 986, DE-A-40 14 987 and DE-A-40 14 988).

It is also known that certain 2-acyl-3-hydroxycyclohex-2-en-1-ones have a regulatory effect on plant growth (U.S. Pat. Nos. 4,560,403, 4,584,013, 4,640,706, EP-A-177 450, EP-A-199 658, EP-A-293 817).

EP-A-123 001, 126 713 and 338 525 disclose since [sic] cyclohexanetriones having an alkoxycarbonyl or dialkylaminocarbonyl group on the cyclohexanedione ring have growth-retarding properties.

Furthermore, BE 833 488, J5 7045143, J5 1013750, J5 7046943, J5 4016454, J5 1131856, DE-A-24 61 027, DE-A-24 39 104 and U.S. Pat. No. 4,011,256 disclose cyclohexenone oxime ethers which have an alkoxycarbonyl or dialkylaminocarbonyl group on the cyclohexanedione ring and possess herbicidal properties.

However, the herbicidal and plant growth-regulating properties of these compounds are satisfactory only to a limited extent, particularly at low application rates and concentrations.

The general terms used in the definition of $R^1$ to $R^8$, halogen, $C_1$–$C_6$-alkyl, $C_1$–$C_4$-alkyl, $C_2$–$C_6$-alkenyl, $C_3$–$C_6$-alkenyl, $C_2$–$C_6$-alkynyl, $C_3$–$C_6$-alkynyl, partially or completely halogenated $C_1$–$C_4$-alkyl, partially or completely halogenated $C_1$–$C_4$-alkoxy, $C_1$–$C_4$-alkoxy, $C_1$–$C_4$-alkylthio, $C_1$–$C_6$-alkylcarbonyl, $C_1$–$C_4$-alkoxy-$C_1$–$C_4$-alkyl, $C_1$–$C_4$-alkylthio-$C_1$–$C_4$-alkyl, $C_1$–$C_4$-alkylsulfinyl, $C_1$–$C_4$-alkylsulfonyl and 5-membered or 6-membered hetaryl having one or two heteroatoms selected from the group consisting of nitrogen, oxygen and sulfur, are abbreviations for a list of the individual group members. All alkyl, alkenyl, alkynyl, haloalkyl or haloalkoxy moieties may be straight-chain or branched. The partially or completely halogenated alkyl or alkoxy moieties may carry identical or different halogen atoms. Specific examples are as follows:

halogen is fluorine, chlorine, bromine or iodine, preferably fluorine or chlorine;

$C_1$–$C_6$-alkyl is methyl, ethyl, n-propyl, 1-methyl-ethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethyl butyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, isopropyl, n-butyl or tert-butyl;

$C_1$–$C_4$-alkyl is methyl, ethyl, n-propyl, isopropyl, n-butyl or tert-butyl;

$C_2$–$C_6$-alkenyl is vinyl or $C_3$–$C_6$-alkenyl, such as prop-1-en-1-yl, prop-2-en-1-yl, 1-methylethenyl, n-but-1-en-1-yl, n-but-1-en-2-yl, n-but-1-en-3-yl, 1-methylprop-1-en-1-yl, 2-methylprop-1-en-1-yl, 1-methylprop-2-en-1-yl, 2-methylprop-2-en-1-yl, n-pent-1-en-1-yl, n-pent-1-en-2-yl, n-pent-1-en-3-yl, n-pent-1-en-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2 -en-1-yl, 1,1-dimethyl-but-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl, preferably prop-2-en-1-yl or but-2-en-1-yl;

$C_2$–$C_6$-alkynyl is ethynyl or $C_3$–$C_6$-alkynyl, such as prop-1-yn-1-yl, prop-2-yn-3-yl, n-but-1-yn-1-yl, n-but-1-yn-4-yl, n-but-2-yn-1-yl, n-pent1-yn-1-yl, n-pent-1-yn-3-yl, n-pent-1-yn-4-yl, n-pent1-yn-5-yl, 3-methylbut-1-yn-1-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably prop-2-yn-1-yl;

$C_3$–$C_6$-cycloalkyl is cyclopropyl, cyclobutyl, cyclopentyl or cyclohexyl, preferably cyclopropyl, cyclopentyl or cyclohexyl;

partially or completely halogenated $C_1$–$C_4$-alkyl is chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2dichloro-2-fluoroethyl, 2,2,2-trichloroethyl, pentafluoroethyl and 3-chloropropyl, preferably trifluoromethyl;

hydroxy-$C_1$–$C_4$-alkyl is hydroxymethyl, 1-hydroxyeth-1-yl, 2-hydroxyeth-1-yl, 1-hydroxyprop-1-yl, 2-hydroxyprop-1-yl, 3-hydroxyprop-1-yl, 1-hydroxyprop-2-yl, 2-hydroxyprop-2-yl, 1-hydroxybut-1-yl, 2-hydroxybut-1-yl, 3-hydroxybut-1-yl, 4-hydroxybut-1-yl, 1-hydroxybut-2-y1,2-hydroxybut-2-yl 1-hydroxybut-3-yl, 2-hydroxybut-3-yl, 1-hydroxy-2-methylprop-3-yl, 2-hydroxy-2-methylprop-3-yl, 3-hydroxy-2-methylprop-3-yl, or 2-hydroxymethylprop-2-yl;

phenyl-$C_1$–$C_4$-alkyl is benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut- 2-yl, 2-phenylbut-2-yl, 3-phenylbut-2-yl, 3-phenylbut-2-yl, 4-phenylbut-2-yl, 1-(phenylmethyl)-eth-1-yl, 1-(phenylmethyl)-1-(methyl)-eth-1-yl or 1-(phenylmethyl)-prop-1-yl;

$C_1$–$C_4$-alkoxy is methoxy, ethoxy, n-propoxy, 1-methylethoxy, n-butoxy, 1-methylpropoxy, 2-methylpropoxy or 1,1-dimethylethoxy, preferably methoxy or ethoxy;

partially or completely halogenated $C_1$–$C_4$alkoxy is difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, preferably trifluoromethoxy;

$C_1$–$C_4$-alkylthio is methylthio, ethylthio, n-propylthio, isopropylthio, n-butylthio or tert-butylthio, preferably methylthio or ethylthio;

$C_1$–$C_4$-alkylthio-$C_1$–$C_4$-alkyl is methylthiomethyl, ethylthiomethyl, n-propylthiomethyl, (1-methylethylthio)-methyl n-butylthiomethyl, (1-methylpropylthio)-methyl, (2-methylpropylthio)-methyl, (1,1-dimethylethylthio)-methyl, methylthioethyl, ethylthioethyl, n-propylthioethyl, (1-methylethylthio)-ethyl, n-butylthioethyl, (1-methylpropylthio)ethyl, (2-methylpropylthio)-ethyl, (1,1-dimethylethylthio)-ethyl, 3-(methylthio)-propyl, 2-(methylthio)-propyl or 2-(ethylthio)-propyl, preferably methylthiomethyl, ethylthiomethyl, 2-methylthioethyl or 2-ethylthioethyl;

$C_1$–$C_4$-alkoxy-$C_1$–$C_4$-alkyl is methoxymethyl, ethoxymethyl, n-propoxymethyl, (1-methylethoxy)-methyl, n-butoxymethyl, (1-methylpropoxy)-methyl, (2-methylpropoxy)-methyl, (1,1-dimethylethoxy)-methyl, methoxyethyl, ethoxyethyl, n-propoxyethyl, (1-methylethoxy)-ethyl, n-butoxyethyl, (1-methylpropoxy)-ethyl, (2-methylpropoxy)-ethyl, (1,1-dimethylethoxy)-ethyl, 3-(methoxy)-propyl, 2-(methoxy)-propyl or 2-(ethoxy)-propyl, preferably methoxymethyl, ethoxymethyl, 2-methoxyethyl or 2-ethoxyethyl;

$C_1$–$C_4$-alkylcarbonyl is methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, preferably methylcarbonyl, ethylcarbonyl, n-propylcarbonyl or 1,1-dimethylethylcarbonyl;

$C_1$–$C_4$-alkylsulfinyl is methylsulfinyl, ethylsulfinyl, n-propylsulfinyl, 1-methylethylsulfinyl, n-butylsulfinyl, 1-methylpropylsulfinyl, 2-methylpropylsulfinyl or 1,1-dimethylethylsulfinyl, preferably methylsulfinyl or ethylsulfinyl;

$C_1$–$C_4$-alkylsulfonyl is methylsulfonyl, ethylsulfonyl, n-propylsulfonyl, 1-methylethylsulfonyl, n-butylsulfonyl, 1-methylpropylsulfonyl, 2-methylpropylsulfonyl and 1,1-dimethylethylsulfonyl, preferably methylsulfonyl and ethylsulfonyl;

a 5-membered or 6-membered aromatic heterocyclic structure having one or two heteroatoms selected from the group consisting of nitrogen, oxygen and sulfur is 2-furyl, 3-furyl, 2-thienyl, 3-thienyl, 2-pyrrolyl, 3-pyrrolyl, 3-isoxazolyl-4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl or 1,2,4-triazin-3-yl.

With regard to the biological activity, preferred cyclohexenone derivatives I are those in which $R^1$, $R^1$ and $R^2$ or $R^1$ and $R^3$ have the following meanings:

$R^1$ is $C_1$–$C_6$-alkyl, in particular methyl, ethyl, n-propyl, isopropyl, n-butyl, isobutyl, sec -butyl, tert-butyl or n-pentyl;

$C_2$–$C_6$-alkenyl or $C_2$–$C_6$-alkynyl, in particular vinyl, propenyl, ethynyl or propynyl; Cyclopropyl, cyclobutyl, cyclopentyl or cyclohexyl; phenyl or pyridyl;

$R^2$ is $C_1$–$C_4$-alkyl, in particular ethyl or n-propyl; partially or completely halogenated $C_1$–$C_3$-alkyl, in particular 2-fluoroethyl or (E)-3-chloroprop-2-en-1-yl;

$C_3$–$C_6$-alkenyl, in particular allyl or (E)-but-2-en-1-yl;

$C_3$–$C_6$-alkynyl, in particular propargyl or but-2-yn-1-yl;

$C_1$–$C_4$-alkyl which carries a 5-membered or 6-membered aromatic heterocyclic structure which has a nitrogen, oxygen or sulfur atom that may in turn be substituted by halogen, in particular 5-chlorothienylmethyl;

$C_3$–$C_6$-alkenyl which carries a phenyl or halophenyl radical, in particular 4-phenylbut-2-en-1-yl, 4-(4-fluorophenyl)-but-2-en-1-yl, 4-(4-chlorophenyl)-but-2-en-1-yl, 4-(4-fluorophenyl)-but-3-en-1-yl or 4-(4-chlorophenyl)-but-3-en-1-yl;

a 3-membered to 6-membered alkyl chain where one chain member is replaced with oxygen and the chain may furthermore additionally carry a phenyl or halophenyl radical, in particular 2-(4-chlorophenoxy)-ethyl, 2-(4-fluorophenoxy)-ethyl, 2-(4-chlorophenoxy)-propyl or 2-(4-fluorophenoxy)-propyl;

$R^3$i s hydrogen;

$C_1$–$C_6$-alkyl, in particular methyl, ethyl, n-propyl, isopropyl, n-butyl, sec -butyl, tert -butyl, n-pentyl or n-hexyl;

$C_3$–$C_6$-alkenyl, in particular allyl; hydroxy-$C_1$- or $C_2$-alkyl, in particular hydroxyethyl;

$C_1$- or $C_2$-alkoxy-$C_1$- or $C_2$-alkyl, in particular 2-methoxyethyl; phenyl or benzyl.

$R^1$ is very particularly preferably methyl, ethyl, n-propyl, n-butyl, cyclopropyl or phenyl;

$R^2$ is very particularly preferably ethyl, allyl, (E)-but-2-en-1-yl, propargyl, but-2-yn-1-yl, (E)-3-chloroprop-2-en-1-yl, 4-(4-fluorophenyl)-but-2-en-1-yl, 4-(4-chlorophenyl)-but-2-en-1-yl, 4-(4-fluorophenyl)-but-3-en-1-yl, 4-(4-chlorophenyl)-but-3-en-1-yl, 2-(4-chlorophenoxy)-propyl, 2-(4-fluorophenoxy)-propyl or 5-chloroethenyl;

$R^3$ is very particularly preferably hydrogen, methyl, ethyl, n-propyl, isopropyl, n-butyl, sec-butyl, isobutyl, n-hexyl, allyl, 2-methoxyethyl, benzyl or phenyl.

Suitable salts of the compounds of the formula I are agriculturally useful salts, for example alkali metal salts, in particular the sodium or potassium salt, alkaline earth metal salts, in particular calcium, magnesium or barium salt, manganese, copper, zinc or iron salts and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

Agriculturally useful esters are understood as meaning the esters of $C_1$–$C_{10}$-fatty acids, in particular $C_1$–$C_6$-alkanecarboxylic acids, such as methanecarboxylic acid (acetic acid), ethanecarboxylic acid (propionic acid), propanecarboxylic acid (butyric acid), 1-methylethanecarboxylic acid (isobutyric acid), butanecarboxylic acid, 1-methylpropanecarboxylic acid, 2-methylpropanecarboxylic acid, 1,1-dimethylethanecarboxylic acid, pentanecarboxylic acid, 1-methylbutanecarboxylic acid, 2-methylbutanecarboxylic acid, 3-methylbutanecarboxylic acid, 1,1-dimethylpropanecarboxylic acid, 1,2-dimethylpropanecarboxylic acid, 2,2-dimethylpropane carboxylic acid, 1-ethylpropanecarboxylic acid, benzoic acid and halogen-substituted benzoic acids, hexanecarboxylic acid, 1-methylpentanecarboxylic acid, 2-methylpentanecarboxylic acid, 3-methylpentanecarboxylic acid, 4-methylpentanecarboxylic acid, 1,1-dimethylbutanecarboxylic acid, 1,2-dimethylbutanecarboxylic acid, 1,3-dimethylbutanecarboxylic acid, 2,2-dimethylbutanecarboxylic acid, 2,3-dimethylbutanecarboxylic acid, 3,3-dimethylbutanecarboxylic acid, 1-ethylbutanecarboxylic acid, 2-ethylbutanecarboxylic acid, 1,1,2-trimethylpropanecarboxylic acid, 1,2,2-trimethylpropanecarboxylic acid, 1-ethyl-1-methylpropanecarboxylic acid and 1-ethyl-2-methylpropanecarboxylic acid, $C_1$–$C_{10}$-sulfonic acids, in particular $C_1$–$C_6$-alkanesulfonic acids, such as methanesulfonic acid, ethanesulfonic acid, propanesulfonic acid, 1-methyl ethanesulfonic acid, butanesulfonic acid, 1-methyl propanesulfonic acid, 2-methylpropanesulfonic acid, 1,1-dimethylethanesulfonic acid, pentanesulfonic acid, 1-methylbutanesulfonic acid, 2-methylbutanesulfonic acid, 3-methylbutanesulfonic acid, 1,1-dimethylpropanesulfonic acid, 1,2-dimethylpropanesulfonic acid, 2,2-dimethylpropanesulfonic acid, 1-ethylpropanesulfonic acid, benzenesulfonic acid and halogen-substituted benzenesulfonic acids, hexanesulfonic acid, 1-methylpentanesulfonic acid, 2-methylpentanesulfonic acid, 3-methylpentanesulfonic acid, 4-methylpentanesulfonic acid, 1,1-dimethylbutanesulfonic acid, 1,2-dimethylbutanesulfonic acid, 1,3-dimethylbutanesulfonic acid, 2,2-dimethylbutanesulfonic acid, 2,3-dimethylbutanesulfonic acid, 3,3-dimethylbutanesulfonic acid, 1-ethylbutanesulfonic acid, 2-ethylbutanesulfonic acid, 1,1,2-trimethylpropanesulfonic acid, 1,2,2-trimethylpropanesulfonic acid, 1-ethyl-1-methylpropanesulfonic acid and 1-ethyl-2-methylpropanesulfonic acid, and $C_1$–$C_{10}$-phosphonic acids, in particular $C_1$–$C_6$-alkanephosphonic acids, such as methanephosphonic acid, ethanephosphonic acid, propanephosphonic acid, 1-methylethanephosphonic acid, butanephosphonic acid, 1-methylpropanephosphonic acid, 2-methylpropanephosphonic acid, 1,1-dimethylethanephosphonic acid, pentanephosphonic acid, 1-methylbutanephosphonic acid, 2-methylbutanephosphonic acid, 3-methylbutanephosphonic acid, 1,1-dimethylpropanephosphonic acid, 1,2-dimethylpropanephosphonic acid, 2,2-dimethylpropanephosphonic acid, 1-ethylpropanephosphonic acid, benzenephosphonic acid and halogen substituted benzenephosphonic acids, hexanephosphonic acid, 1-methylpentanephosphonic acid, 2-methylpentanephosphonic acid, 3-methylpentanephosphonic acid, 4-methylpentanephosphonic acid, 1,1-dimethylbutanephosphonic acid, 1,2-dimethylbutanephosphonic acid, 1,3-dimethylbutanephosphonic acid, 2,2-dimethylbutanephosphonic acid, 2,3-dimethylbutanephosphonic acid, 3,3-dimethylbutanephosphonic acid, 1-ethylbutanephosphonic acid, 2-ethylbutanephosphonic acid, 1,1,2-trimethylpropanephosphonic acid, 1,2,2-trimethylpropanephosphonic acid, 1-ethyl-1-methylpropanephosphonic acid and 1-ethyl-2-methylpropanephosphonic acid.

The cyclohexenone derivatives I are obtainable by various methods, preferably by reacting a 5-substituted cyclohexane-1,3-dione of the formula II with an acid derivative of the formula III:

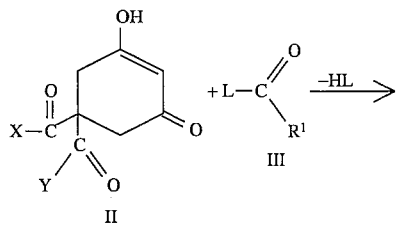

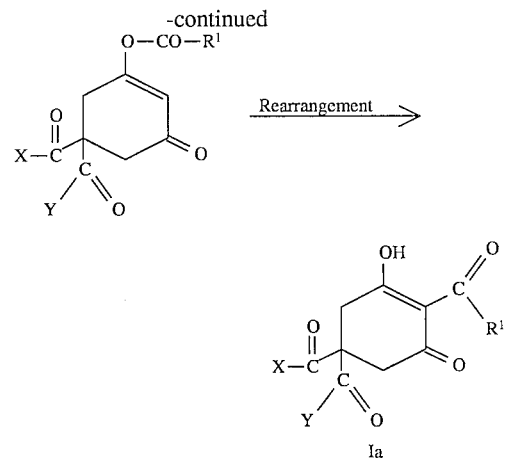

L is a nucleophilic leaving group, in particular a halide ion, such as chloride or bromide.

Another possible method for synthesizing cyclohexenone derivatives Ia from the cyclohexane-1,3-diones II is described in Tetrahedron Letters, (1975) 2491.

The 5-substituted cyclohexenone-1,3-diones [sic] of the formula II can be advantageously prepared in a conventional manner by cyclization of compounds of the general formula VI:

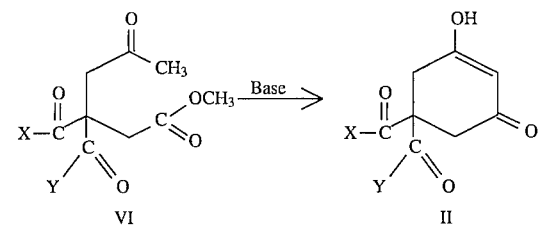

The cyclization is carried out in the presence of a strong base, for example of an alkali metal hydride, such as sodium hydride, of a lithium organyl, such as butyllithium, or of an alkali metal amide, such as lithium diisopropylamide or sodium amide.

The reaction is advantageously carried out in homogeneous or heterogeneous phase in an inert solvent or diluent.

Examples of suitable solvents are dimethyl sulfoxide, dimethylformamide, N-methylpyrollidone [sic], aromatic hydrocarbons, such as benzene and toluene, aliphatic hydrocarbons, such as hexane and cyclohexane, or ethers, such as dioxane and tetrahydrofuran.

In general, the reaction temperature is from –100° C. to the boiling point of the reaction mixture, preferably from –70° to 40° C.

The compounds of the formula VI can be prepared by syntheses similar to those described in Izv. Akad. Nauk SSSR, Ser. Khim. 2 (1990), 473–474.

Cyclohexenone derivatives of the formula Ib can be obtained in a conventional manner from the cyclohexenone derivatives Ia (cf. DE-A-34 33 767):

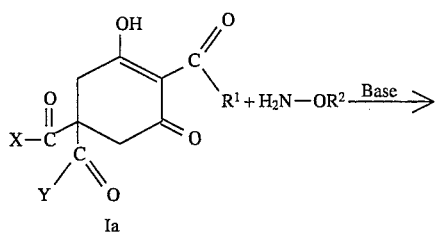

Ia

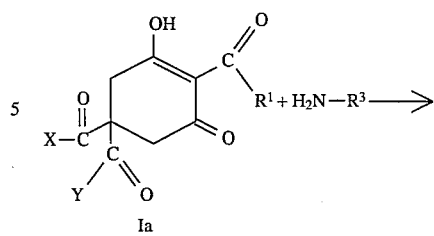

Ia

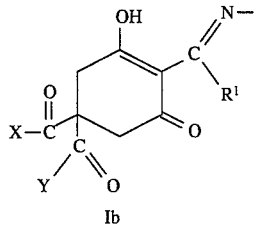

Ib

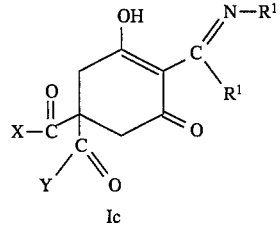

Ic

The reaction can be carried out both with the hydroxylamine $H_2N$—$OR_2$, preferably in the form of an aqueous solution, and with one of its salts.

A suitable salt of the hydroxylamine $H_2N$—$OR^2$, in particular its hydrochloride, is preferably used, and the reaction is carried out in the heterogeneous phase in an inert diluent, for example in dimethyl sulfoxide, in an alcohol, such as methanol, ethanol or isopropanol, in an aromatic hydrocarbon, such as benzene or toluene, in a chlorohydrocarbon, such as chloroform or 1,2-dichloroethane, in an aliphatic hydrocarbon, such as hexane or cyclohexane, in an ester, such as ethyl acetate, or in an ether, such as dioxane or tetrahydrofuran.

When the reaction is carried out using an aqueous solution of the hydroxylamine $H_2N$—$OR^2$, a one-phase or two-phase reaction mixture is obtained, depending on the solvent used for the cyclohexenone derivative Ia. Suitable solvents for this purpose are, for example, alcohols, such as methanol, ethanol and isopropanol, aromatic hydrocarbons, such as benzene and toluene, chlorohydrocarbons, such as chloroform and dichloroethane, aliphatic hydrocarbons, such as hexane and cyclohexane, esters, such as ethyl acetate, ethers, such as dioxane and tetrahydrofuran, and nitriles, such as acetonitrile.

The reaction is carried out in the presence of a base, for example the carbonates, bicarbonates, acetates, alcoholates, hydroxides or oxides of alkali metals and alkaline earth metals, preferably sodium hydroxide, potassium hydroxide, magnesium oxide or calcium oxide, being suitable. Organic bases, for example tertiary amines, such as triethylamine and pyridine, are also suitable.

The cyclohexenone derivative Ia and the hydroxylamine $H_2N$—$OR^2$ or its salt are usually used in a stoichiometric ratio, but in some cases an excess of up to about 10 mol% of one or other component may be advantageous. The amount of base is not critical; as a rule, an amount from 0.5 to 2 mol, based on the amount of the hydroxylamine $H_2N$—$OR^2$, is sufficient.

The reaction temperature is in general from 0° C. to the boiling point of the reaction mixture, preferably from 20° to 80° C.

Cyclohexanetriones of the formula Ic can be prepared in a conventional manner by reacting a cyclohexenone derivative Ia with an amine $H_2N$—$R^3$:

As a rule, the reaction is carried out in the homogeneous phase in an inert solvent.

Suitable solvents are, for example, dimethyl sulfoxide, alcohols, such as methanol, ethanol and isopropanol, aromatic hydrocarbons, such as benzene and toluene, chlorohydrocarbons, such as chloroform and 1,2-dichloroethane, aliphatic hydrocarbons, such as hexane and cyclohexane, esters, such as ethyl acetate, and ethers, such as dioxane and tetrahydrofuran.

The starting materials are advantageously used in roughly stoichiometric ratio, but in some cases an excess of up to about 10 mol% of one or other component may be advantageous.

In general, a reaction temperature of from 0° C. to the boiling point of the reaction mixture, preferably from 20° to 80° C., is employed.

All of the abovementioned reactions are advantageously carried out at atmospheric pressure. Lower or higher pressure is possible but generally has no advantages.

The particular reaction mixtures are worked up to obtain the products by means of a conventional working-up method, preferably by evaporating the mixture, partitioning the residue in methylene chloride/water and distilling off the solvent under reduced pressure.

The novel cyclohexenone derivatives can form salts of alkali metal or alkaline earth metal compounds and enol esters.

By treating the compounds Ia, Ib or Ic with sodium hydroxide, potassium hydroxide, sodium alcoholate or potassium alcoholate in aqueous solution or in an organic solvent, for example in an alcohol, such as methanol or ethanol, an aromatic hydrocarbon, such as toluene, or an aprotic solvent, such as acetone, alkali metal salts of the cyclohexenone derivatives I can be prepared.

Other metal salts, for example the manganese, copper, zinc, iron, calcium, magnesium and barium salts, can be prepared from the sodium salts of the cyclohexenone derivatives Ia or Ib in a conventional manner, as can ammonium, phosphonium, sulfonium or sulfoxonium salts by means of ammonia or phosphonium, sulfonium or sulfoxonium hydroxides.

The cyclohexenone derivatives I may be obtained in the preparation as isomer mixtures, both E/Z isomer mixtures and enantiomer or diastereomer mixtures being possible. The isomer mixtures can, if desired, be separated by the conventional methods, for example by chromatography or by crystallization.

The cyclohexenone derivatives I can be represented in a plurality of tautomeric forms, and the present invention relates to all of these.

Both as isomer mixtures and in the form of the pure isomers, the cyclohexenone derivatives Ib are suitable as herbicides, in particular for controlling plant species from the Gramineae family (grasses). In general, they are tolerated and thus selective in broad-leaved crops and in monocotyledon plants.

Depending on the particular application method, the cyclohexenone derivatives Ib or the agents containing them can be used for eliminating undesirable plants in a large number of crops, the following crops being mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Brassica napus* var. *napus* | rapeseed |
| *Brassica napus* var. *napobrassica* | swedes |
| *Brassica rapa* var. *silvestris* | turnip rape |
| *Camellia sinensis* | tea plants |
| *Carthamus tinctorius* | safflower |
| *Carya illinoinensis* | pecan trees |
| *Citrus limon* | lemons |
| *Citrus sinensis* | orange trees |
| *Coffea arabica* (*Coffea, canephora, Coffea liberica*) | coffee plants |
| *Cucumis sativus* | cucumbers |
| *Cynodon dactylon* | Bermudagrass |
| *Daucus carota* | carrots |
| *Elaeis* [sic] *guineensis* | oil palms |
| *Fragaria vesca* | strawberries |
| *Glycine max* | soybeans |
| *Gossypium hirsutum* (*Gossypium arboreum, Gossypium herbaceum, Gossypium vitifolium*) | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Musa* spp. | banana plants |
| *Nicotiana tabacum* (*N. rustica*) | tobacco |
| *Olea europaea* | olive trees |
| *Phaseolus lunatus* | limabeans |
| *Phaseolus vulgaris* | snapbeans, green beans, dry beans |
| *Picea abies* | Norway spruce |
| *Pinus* spp. | pine trees |
| *Pisum sativum* | English peas |
| *Prunus avium* | cherry trees |
| *Prunus persica* | peach trees |
| *Pyrus communis* | pear trees |
| *Ribes sylvestre* | redcurrants |
| *Ricinus communis* | castor-oil plants |
| *Saccharum officinarum* | sugar cane |
| *Secale cereale* | rye |
| *Solanum tuberosum* | Irish potatoes |
| *Sorghum bicolor* (*S. vulgare*) | sorghum |
| *Theobroma cacao* | cacao plants |
| *Trifolium pratense* | red clover |
| *Triticum aestivum* | wheat |
| *Triticum durum* | durum wheat |
| *Vicia faba* | tick beans |
| *Vitis vinifera* | grapes |
| *Zea mays* | Indian corn, sweet corn, maize |

The cyclohexenone compounds of the formula Ia and Ic may influence the various plant development stages, and are therefore used as growth regulators. The diversity of action of the plant growth regulators depends especially on a) the type and variety of plants, b) the time applied, with reference to the development stage of the plants, and the time of the year, c) the place and method of application (eg. seed treatment, soil treatment, application to foliage, or trunk injection in the case of trees), d) climatic factors (eg. temperature, amount of precipitation, and also daylength and light intensity), e) soil conditions (including fertilization), f) the formulation or application form of the active ingredient, and g) the concentrations at which the active ingredients are applied.

A description of some of the various possibilities of using the plant growth regulators of the formula I according to the invention in agriculture and horticulture is given below.

A. The compounds which can be used according to the invention allow vegetative plant growth to be inhibited to a considerable extent, a fact which is manifested particularly in a reduction in plant height. The treated plants thus have a compact habit, furthermore, the leaf color is darker.

A practical advantage is a reduction in grass growth on roadsides, hedges, canal embankments and in grassy areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions before harvesting.

The use of growth regulators is also important for inhibiting plant height and changing the time of ripening in cotton. It is thus possible for this important crop to be harvested completely mechanically.

Costs relating to the pruning of fruit trees and other trees can be reduced with the growth regulators. Growth regulators can also be used to break up the alternate breeding rhythm of fruit trees.

Growth regulators may also increase or inhibit lateral branching of the plants. This is of interest when, for instance in tobacco plants, it is desired to inhibit the formation of lateral shoots (suckers) in favor of leaf growth.

Growth regulators also considerably increase the resistance of, for example, winter rape to frost. On the one hand, upward growth and the development of a too luxuriant (and thus particularly frost-susceptible) leaf or plant mass are inhibited; on the other, after sowing and before the onset of winter frosts, the young rape plants are kept in the vegetative development stage in spite of favorable growth conditions. The danger of freeze injury is thus also eliminated in plants which tend to lose prematurely their inhibition to bloom and pass into the generative phase. In other crops, too, eg. winter cereals, it is advantageous if the plants are well tillered in the fall as a result of treatment with compounds according to the invention, but enter winter with not too lush a growth. This is a preventive measure against increased susceptibility to freeze injury and—because of the relatively low leaf or plant mass—attack by various (especially fungal) diseases. The inhibition of vegetative growth also makes closer planting possible in numerous crops, which means an increase in yield, based on the area cropped.

B. Better yields both of plant parts and plant materials may be obtained with the growth regulators. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The compounds of the formula I may raise the yield by influencing plant metabolism or by promoting or inhibiting vegetative and/or generative growth.

C. Finally, it is also possible with plant growth regulators to shorten or lengthen development stages and to accelerate or retard the ripening process in the harvested plant parts either before or after harvesting.

A factor of economic interest is for example the facilitation of harvesting made possible by a temporally concentrated loosening (abscission) or reduction of the adherence of stalks to the branches of citrus fruit, olive trees, and other kinds of pomes, drupes and indehiscent fruit. The same mechanism, ie. promotion of the formation of separation layers between fruit or leaf and stem of the plant, is also essential for a readily controllable defoliation of crop plants, eg. cotton.

D. Furthermore, transpiration in plants may be reduced with growth regulators. This is particularly important for agriculturally viable areas which are expensive to irrigate by artificial means, eg. arid or semi-arid areas. Irrigation frequency can be reduced by using the ingredients according to the invention, making for lower costs. Under the influence of growth regulators, the water available can be better utilized, because, inter alia, the size of the stomata opening is reduced, a thicker epidermis and cuticle are formed, penetration of the soil by the roots is improved, and the microclimate in the stand is favorably influenced by a more compact growth.

The cyclohexenone compounds Ia and Ic are particularly suitable for shortening stem length in crops such as barley, rape and wheat.

The growth regulators of the formula Ia and Ic to be used according to the invention may be applied to the crops not only via the seed (as a dressing), but also via the soil, ie. through the roots, and—particularly preferably—via the foliage by spraying.

As a result of the active ingredient being well tolerated by plants, the application rate is not critical. The optimum application rate varies, depending on the objective to be achieved, the time of the year, the plants to be controlled and the growth stage.

The active ingredients Ia, Ib and Ic may be applied as such, in the form of their formulations or the application forms prepared therefrom, for instance in the form of directly sprayable solutions, powders, suspensions, dispersions, emulsions, oil dispersions, pastes, dusts, broadcasting agents or granules by spraying, atomizing, dusting, broadcasting or watering. The forms of application depend entirely on the intended uses, but they must in any event ensure as fine a distribution of the active ingredients according to the invention as possible.

The formulations are produced in known manner, for example by extending the active ingredient with solvents and/or carriers, with or without the use of emulsifiers and dispersants; if water is used as diluent, it is also possible to employ other organic solvents as auxiliary solvents. Suitable inert auxiliaries for this purpose are in the main: mineral oil fractions of medium to high boiling point, such as kerosene and diesel oil, coal-tar oils and oils of vegetable or animal origin; solvents such as aromatics (eg. xylene, toluene), chlorinated aromatics (eg. chlorobenzenes), paraffins (eg. crude oil fractions), alcohols (eg. methanol, ethanol, butanol, cyclohexanol), ketones (eg. cyclohexanone, isophorone), amines (eg. ethanolamine, N,N-dimethylformamide, N-methylpyrrolidone) and water; carriers such as ground natural minerals (eg. kaolins, aluminas, talc, chalk) and ground synthetic materials (eg. highly disperse silica, silicates); emulsifiers such as nonionic and anionic emulsifiers (eg. polyoxyethylene-fatty alcohol ethers, alkylsulfonates and arylsulfonates); and dispersants such as ligninsulfite waste liquors and methylcellulose.

Aqueous application forms may be prepared from emulsion concentrates, dispersions, pastes, wettable powders or water-dispersible granules by adding water. To prepare emulsions, pastes or oil dispersions, the substrates [sic] as such or dissolved in an oil or solvent may be homogenized in water by means of wetting agents, adherents, dispersants or emulsifiers. Furthermore, however, concentrates which are suitable for dilution with water may be prepared from active ingredient, wetting agent, adherent, dispersant or emulsifier and possibly a solvent or oil.

Examples of surfactants are alkali metal, alkaline earth metal and ammonium salts of aromatic sulfonic acids, eg. ligninsulfonic acid, phenolsulfonic acid, naphthalenesulfonic acid and dibutylnaphthalenesulfonic acid, and of fatty acids, and alkylsulfonates, alkylarylsulfonates, alkylsulfates, lauryl ether sulfates, fatty alcohol sulfates, salts of sulfated hexadecanols, heptadecanols and octadecanols, salts of fatty alcohol glycol ethers, condensation products of sulfonated naphthalene and napthalene derivatives with formaldehyde, condensation products of naphthalene or naphthalenesulfonic acids with phenol and formaldehyde, polyoxyethylene octylphenol ethers, ethoxylated isooctylphenol, octylphenol or nonylphenol, alkylphenol polyglycol ethers, tributylphenyl polyglycol ethers, alkylaryl polyether alcohols, isotridecyl alcohol, fatty alcoholethylene oxide condensates, ethoxylated castor oil, polyoxyethylene alkyl ethers or polyoxypropylene, lauryl alcohol polyglycol ether acetate [sic], sorbitol esters, lignin-sulfite waste liquors and methylcellulose.

Powders, dusts and broadcasting agents may be prepared by mixing or grinding the active ingredients together with a solid carrier.

Granules, e.g., coated, impregnated or homogeneous granules, may be prepared by bonding the active ingredients to solid carriers. Examples of solid carriers are mineral earths such as silica gel, silicic acids, silica gels [sic], silicates, talc, kaolin, limestone, lime, chalk, bole, loess, clay, dolomite, diatomaceous earth, calcium sulfate, magnesium sulfate and magnesium oxide, ground plastics, fertilizers such as ammonium sulfate, ammonium phosphate, ammonium nitrate and ureas, and vegetable products such as grain meals, bark meal, wood meal, nutshell meal and cellulosic powders, etc.

The concentrations of active ingredients Ia, Ib and Ic in the ready-to-use formulations may vary within wide ranges—from about 0.01 to 95, preferably from 0.5 to 90% by weight of active ingredient. The active ingredients are used in a purity of 90 to 100, preferably 95 to 100% (based on the NMR spectrum).

Examples of such formulations are given below:

I. A solution of 90 parts by weight of compound No. 1.1 and 10 parts by weight of N-methyl-a) pyrrolidone [sic], which is suitable for application in the form of very fine drops.

II. A mixture of 20 parts by weight of compound No. 1.2, 80 parts by weight of xylene, 10 parts by weight of the adduct of 8 to 10 moles of ethylene oxide and I mole of oleic acid N-monoethanolamide, 5 parts by weight of the calcium salt of dodecylbenzenesulfonic acid, and 5 parts by weight of the adduct and [sic] 40 moles of ethylene oxide and I mole of castor oil. By finely dispersing the mixture in 100,000 parts by weight of water, a dispersion containing 0.02 % by weight of the active ingredient is obtained.

III. An aqueous dispersion of 20 parts by weight of compound No. 1.1, 40 parts by weight of cyclo hexanone, 30 parts by weight of isobutanol, 20 parts by weight of the adduct of 40 moles of ethylene oxide and I mole of castor oil. A mixture of this dispersion with 100,000 parts by weight of water contains 0.02 % by weight of the active ingredient.

IV. An aqueous dispersion of 20 parts by weight of compound No. 1.2, 25 parts by weight of cyclohexanol, 65 parts by weight of a mineral oil fraction having a boiling point of from 210 to 280° C., and 10 parts by weight of the adduct of 40 moles of ethylene oxide and 1 mole of castor oil. A mixture of this dispersion with 100,000 parts by weight of water contains 0.02 % by weight of the active ingredient.

V. A hammer-milled mixture of 80 parts by weight of compound No. 1.1, 3 parts by weight of the sodium salt of diisobutylnapthalene-a-sulfonic [sic] acid, 10 parts by weight of the sodium salt of a lignin-sulfonic acid obtained from a sulfite waste liquor, and 7 parts by weight of powdered silica gel. By finely dispersing the mixture in 20,000 parts by weight of water, a spray liquor containing 0.1% by weight of the active ingredient is obtained.

VI. An intimate mixture of 3 parts by weight of compound No. 1.2 and 97 parts by weight of particulate kaolin. This dust contains 3 % by weight of the active ingredient.

VII. An intimate mixture of 30 parts by weight of compound No. 1.1, 92 parts by weight of powdered silica gel and 8 parts by weight of paraffin oil sprayed onto the surface of this silica gel. This formulation gives the active ingredient good adherence.

VIII. A stable aqueous dispersion of 40 parts by weight of compound No. 1.2, 10 parts by weight of the sodium salt of a phenolsulfonic acid-urea) formaldehyde condensate, 2 parts by weight of silica gel and 48 parts by weight of water, which dispersion can be further diluted.

IX. A stable oily dispersion of 20 parts by weight of compound No. 1.1, 2 parts by weight of the calcium salt of dodecylbenzenesulfonic acid, 8 parts by weight of a fatty alcohol polyglycol ether, 20 parts by weight of the sodium salt of a phenolsulfonic acid-urea-formaldehyde condensate and 68 parts by weight of a paraffinic mineral oil.

X. A hammer-milled mixture of 10 parts by weight of compound No. 1.2, 4 parts by weight of the sodium salt of diisobutylnaphthalene-a-sulfonic [sic] acid, 20 parts by weight of the sodium salt of a lignin-sulfonic acid obtained from a sulfite waste liquor, 38 parts by weight of silica gel and 38 parts by weight of kaolin. By finely dispersing the mixture in 10,000 parts by weight of water, a spray liquor containing 0.1 % by weight of the active ingredient is obtained.

The active ingredients or the herbicidal and plant growth-regulating agents may be applied pre- or postemergence. Normally, the plants are sprayed or dusted with the active ingredients or the seeds of the test plants are treated with the active ingredients. If the active ingredients are less well tolerated by certain crops, application techniques may be used in which the herbicidal agents are sprayed from suitable equipment in such a manner that the leaves of sensitive crops are if possible not affected, while the active ingredients reach undesirable plants growing beneath the crops or the uncovered soil surface (post-directed, lay-by treatment).

Depending on the objective to be achieved, the time of the year, the plants to be controlled and their growth stage, the active ingredient is applied at rates of from 0.001 to 5.0, preferably 0.01 to 2, kg/ha.

To increases the spectrum of action and to achieve synergistic effects, the cyclohexenone derivatives I may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1, 3-dione derivatives bearing, for example, a carboxy or carbimino group in the 2position, quinolinecarboxylic acid derivatives, imidazolinones, sulfonamides, sulfonylureas, (het)aryloxyphenoxyphenoxypropionic acids and salts, esters and amides thereof, etc.

The cyclohexenone derivatives Ia, Ib and Ic may also be applied together with other crop protection agents such as herbicides, growth regulators, pesticides, fungicides and bactericides. These agents may be added to the agents according to the invention in a weight ratio of from 1:100 to 100:1, if desired immediately prior to use (tankmix). It may also be of interest to mix the compounds with solutions of mineral salts used to remedy nutritional or trace element deficiencies. Non-phytotoxic oils and oil concentrates may also be added.

PREPARATION EXAMPLES

Example 1

Diethyl 1 4-cyclopropylcarbonyl-3,5-dioxocyclohexane-1,1dicarboxylate (compound No. 1.1)

0.1 g of dimethylaminopyridine were [sic] added to a solution of 1.2 g of diethyl 3-cyclopropylcarbonyloxy-5-oxocyclohex-3-ene-1,1-dicarboxylate in 20 ml of dichloromethane. The reaction mixture was then stirred at 20°–25° C. for 4 days. The solvent was then removed under reduced pressure and the residue was purified chromatographically (developer: cyclohexane/ethyl acetate 8:2 to 1:2). Yield: 0.6 g.

Preliminary stage1a)
Ethyl 2-carbethoxy-4-oxo-valerate

While stirring rapidly, 15 g (0.162 mol) of chloroacetone were added dropwise to a mixture of 9 g (0.162 mol) of finely powdered potassium hydroxide, 24.7 ml (0.162 mol) of diethylmalonate, approx. 0.2 g of benzyltriethylammonium chloride and 150 ml of dimethylformamide. Upon completion of the exothermic reaction, the mixture was stirred for a further 2 to 3 hours at 45° C. and then allowed to cool to 20°–25° C. The reaction products were then partitioned between ethyl acetate and water, after which the organic phase was washed 3 times, each time with 100 ml of water, dried over sodium sulfate and evaporated down. Yield: 30.6 g of an oil which contains about 61% of the product according to analysis by gas chromatography. The product was purified by fractional distillation (bp$_{0.1\ mm}$ $_{Hg}$:87°–88° C.).

$^1$H-NMR (in CDCl$_3$; TMS as internal standard): δ=1.3 ppm (t,6H); 2.2 ppm (s,3H); 3.08 ppm (d,2H); 3.88 ppm (t,1H); 4.22 ppm (q,4H).

Preliminary stage 1b)

Ethyl 3,3-biscarbethoxy-5-oxo-hexanecarboxylate 4 ml (0.037 mol) of ethyl chloroacetate were added dropwise to a suspension of 2.1 g (0.037 mol) of finely powdered potassium hydroxide, 8 g (0.037 mol) of ethyl 2-carbethoxy-4-oxo-valerate, approx. 0.1 g of benzyltriethylammonium chloride and 150 ml of dimethylformamide. After about 15 hours' stirring at 20°–25° C., 2 ml (0.017 mol) of ethyl chloroacetate and 1 g (0.016 mol) of potassium hydroxide were again added to complete the reaction. The mixture was again stirred at 20°–25° C. for 2 hours, after which the reaction products were partitioned between ethyl acetate and 20 % strength by weight ammonium chloride solution. The organic phase was washed twice, each time with 50 ml of 20 % strength by weight ammonium chloride solution, then dried and evaporated down. Yield: 9.5 g of an oil containing 91% of the product. Purification was effected by fractional distillation (bp$_{0.1\ mm\ HG}$: 135° C.).

$^1$H-NMR (in CDCl$_3$; TMS as internal standard): 1.25 ppm (t,9H); 2.15 ppm (s,3H); 3.13 ppm (s,2H), 3.35 ppm (s, 2H); 4.05–4.3 ppm (m, 6H).

Preliminary stage 1c)

5,5-Biscarbethoxy-cyclohexane-1,3-dione

A solution of 14.3 g (0.047 mol) of ethyl 3,3-biscarbethoxy-5-oxo-hexanecarboxylate in 40 ml of dimethylformamide was added dropwise to a suspension of 3.6 g (0.118 mol) of 80 % strength by weight sodium hydride in 200 ml of dimethylformamide. After stirring at 20°–25° C. for about 15 hours, the reaction was stopped by adding 5 ml of isopropanol. The reaction products were partitioned between ethyl acetate and 1 molar hydrochloric acid. The organic phase was then separated, dried and evaporated down. Yield: 2.2 g of a crude product oil.

$_1$H-NMR (in CDCl$_3$; TMS as internal standard); δ=1.28 ppm (t,6H); 2.98 ppm (s,4H); 4.25 ppm (q,4H); 5.5 ppm (s,1H); 9.2 ppm (bs,1H).

Preliminary stage 1d)

Diethyl 3-cyclopropylcarbonyloxy-5-oxo-cyclohex-3-ene-1,1-dicarboxylate 0.94 g (9.4 mmol) of triethylamine was added to a solution of 2.4 g (9.4 mmol) of 5,5-biscarbethoxy-cyclohexane-1,3-dione in 25 ml of anhydrous tetrahydrofuran. A solution of 0.98 g (9.4 mmol) of cyclopropanecarboxylic chloride in 5 ml of tetrahydrofuran was added dropwise to this mixture at 0° to 10° C. After the mixture had been stirred at 0° to 10° C. for about 1 hour, no more starting material could be detected by thin-layer chromatography. Subsequently, the solvent was removed and the residue was taken up in ethyl acetate. The organic phase was washed twice with 1% strength acetic acid and twice with water, dried and evaporated down. The tube [sic] product was purified chromatographically (developer: cyclohexane/ethyl acetate 8:2). Yield: 1.2 g.

Table 1 below lists further compounds I which were, or can be, prepared in the same manner.

TABLE 1

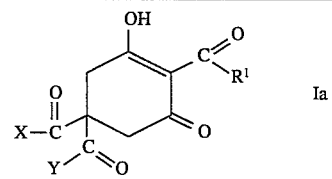

Ia

| No. | R$^1$ | X | Y | $^1$H-NMR (δ [ppm], in CDCl$_3$) |
|---|---|---|---|---|
| 1.1 | cyclopropyl | O-ethyl | O-ethyl | 1.15 (m, 2H); 1.27 (t, 3H); 1.3 (m, 2H); 3.0 (s, 2H); 3.18 (s, 2H); 3.55 (m, 1H); 4.25 (q, 4H); |
| 1.2 | ethyl | O-ethyl | O-ethyl | 1.1 (t, 3H); 1.25 (t, 6H); 2.96 (s, 2H); 3.08 (q, 2H); 3.18 (s, 2H); 4.25 (q, 4H); |
| 1.3 | ethyl | O-methyl | O-methyl | 1.14 (t, 3H); 2.99 (s, 2H); 3.07 (q, 2H); 3.21 (s, 2H); 3.78 (s, 6H); |
| 1.4 | methyl | O-methyl | O-methyl | 2.59 (s, 3H); 2.98 (s, 2H); 3.2 (s, 2H); 3.75 (s, 6H); |
| 1.5 | cyclopropyl | O-methyl | O-methyl | 1.17 (m, 2H); 1.33 (m, 2H), 3.02 (s, 2H); 3.18 (s, 2H); 3.55 (m, 1H); 3.77 (s, 6H); |
| 1.6 | propyl | O-methyl | O-methyl | 0.97 (t, 3H); 1.62 (m, 2H); 2.97 (m, 4H); 3.2 (s, 2H); 3.76 (s, 6H); |
| 1.7 | 4-chlorophenyl | O-methyl | O-methyl | 3.13 (bs, 4H); 3.83 (s, 6H), 7.4 (d, 2H); 7,48 (d, 2H); |
| 1.8 | 4-chloro-2-nitrophenyl | O-methyl | O-methyl | 2.84 (s, 2H); 3.33 (s, 2H); 3.79 (s, 6H); 7.21 (d, 1H); 7.68 (dd, 1H); 8.19 (d, 1H); |
| 1.9 | 4-chlorophenyl | OH | O-methyl | 3.0 (bs, 4H); 3.74 (s, 3H), 7.55 (d, 3H); 7.69 (d, 2H); |

TABLE 2 where X and Y are each O-methyl

| No. | R¹ | R² | ¹H-NMR |
|---|---|---|---|
| 2.1 | methyl | i-propyl | 1.29 (d, 6H); 2.56 (s, 3H); 2.99 (s, 4H), 3.73 (s, 6H); 3.97 (m, 1H); |
| 2.2 | methyl | i-butyl | 1.09 (d, 6H); 1.96 (m, 1H); 2.52 (s, 3H): 2.98 (s, 4H); 3.22 (t, 2H); 3.74 (s, 6H); |
| 2.3 | methyl | s-butyl | 0.96 (t, 3H); 1.26 (d, 3H); 1.65 (m, 2H); 2.53 (s, 3H); 3.0 (s, 4H); 3.73 (m, 7H); |
| 2.4 | ethyl | i-propyl | 1.19 (s, 3H); 1.3 (d, 6H); 2.99 (s, 4H); 3.02 (q, 2H); 3.75 (s, 6H), 4.06 (m, 1H); |
| 2.5 | ethyl | s-butyl | 0.95 (t, 3H); 1.17 (t, 3H); 1.28 (d, 3H); 1.64 (m, 2H); 2.99 (m, 6H); 3.72 (s, 6H); |
| 2.6 | ethyl | i-butyl | 1.04 (d, 6H), 1.17 (t, 3H); 1.98 (m, 1H); 3.0 (m, 6H); 3.25 (m, 2H); 3.75 (s, 6H); |
| 2.7 | propyl | i-propyl | 1.04 (t, 3H); 1.29 (d, 6H); 1.52 (m, 2H); 2.96 (m, 6H); 3.75 (s, 6H); 3.72 (m, 1H); |
| 2.8 | propyl | s-butyl | 0.94 (m, 3H); 1.05 (t, 3H); 1.28 (d, 3H); 1.62 (m, 4H); 2.97 (m, 6H); 3.72 (m, 7H); |
| 2.9 | propyl | i-butyl | 0.94 (m, 3H); 1.05 (d, 6H); 1.54 (m, 2H); 1.96 (m, 1H); 2.94 (m, 2H); 2.97 (s, 4H); 3.25 (m, 2H); 3.73 (s, 6H); |
| 2.10 | methyl | benzyl | 2.69 (s, 3H); 2.99 (s, 4H); 3.73 (s, 6H); 4.58 (d, 2H); 7.27 (m, 5H); |

TABLE 3 where X and Y are each O-methyl

| No. | R¹ | R² | ¹H-NMR |
|---|---|---|---|
| 3.1 | methyl | ethyl | 1.32 (s, 3H); 2.39 (s, 3H); 3.02 (s, 4H); 3.78 (s, 6H); 4.11 (q, 2H); |
| 3.2 | methyl | allyl | 2.38 (s, 3H); 2.92 (bs, 2H); 3.13 (bs, 2H); 3.74 (s, 6H); 4.52 (d, 2H); 5.38 (m, 2H), 5.98 (m, 1H); |
| 3.3 | methyl | t-chloroallyl | 2.34 (s, 3H); 3.03 (bs, 4H); 3.74 (s, 6H), 4.54 (d, 2H); 6.11 (m, 1H); 6.32 (d, 1H); |
| 3.4 | methyl | 2-(4-chlorophenoxy)propyl | 1.34 (d, 3H); 2.29 (s, 3H); 2.9 (bs, 2H); 3.14 (bs, 2H), 3.75 (s, 6H); 4.19 (m, 2H); 4.59 (m, 1H); 6.87 (d, 2H); 7.20 (d, 2H); |
| 3.5 | ethyl | ethyl | 1.1 (t, 3H); 1.34 (t, 3H); 2.97 (q, 2H); 3.04 (m, 4H); 3.75 (s, 6H); 4.1 (q, 2H) |
| 3.6 | ethyl | allyl | 1.09 (t, 3H); 2.9 (q, 2H); 3.78 (s, 6H); 4.54 (d, 2H); 5.35 (m, 2H); 5.92 (m, 1H); |
| 3.7 | ethyl | t-chloroallyl | 1.07 (t, 3H); 2.86 (q, 2H); 3.74 (s, 6H); 4.5 (d, 2H); 6.12 (m, 1H); 6.34 (d, 1H); |
| 3.8 | ethyl | 2-(4-chlorophenoxy)propyl | 1.04 (t, 3H); 1.33 (d, 3H); 2.82 (q, 2H); 2.94 (m, 2H); 3.16 (m, 2H); 3.78 (s, 6H); 4.2 (m, 2H); 4.6 (m, 1H); 6.88 (d, 2H); 7.2 (d, 2H); |
| 3.9 | propyl | ethyl | 0.95 (t, 3H); 1.34 (t, 3H); 1.5 (m, 2H); 2.94 (m, 2H); 3.04 (s, 4H); 3.74 (s, 6H); 4.13 (q, 2H); |
| 3.10 | propyl | alkyl | 0.94 (t, 3H); 1.5 (m, 2H); 2.93 (m, 2H); 3.04 (bs, 4H); 3.79 (s, 6H); 4.55 (d, 2H); 5.38 (m, 2H); 5.97 (m, 1H); |
| 3.11 | propyl | t-chloroalkyl | 0.92 (t, 3H); 1.46 (m, 2H); 2.9 (m, 4H); 3.15 (m, 2H); 3.76 (s, 6H); 4.52 (d, 2H); 6.09 (m, 1H); 6.33 (d, 1H); |
| 3.12 | propyl | 2-(4-chlorophenoxy)propyl | 0.87 (t, 3H); 1.31 (d, 3H); 1.45 (m, 2H); 2.9 (m, 4H); 3.14 (m, 2H); 3.76 (s, 6H); 4.19 (m, 2H); 4.60 (m, 1H); 6.83 (d, 2H); 7.2 (d, 2H); |

Use examples

The herbicidal and plant growth-regulating action of the substituted cyclohexenones I, Ia and Ib is demonstrated by greenhouse experiments:

The plants were grown in plastic flowerpots containing sandy loam with about 3.0 % humus as substrate. The seeds of the test plants were sown separately, according to species.

For the preemergence treatment, the active ingredients, suspended or emulsified in water, were applied directly after sowing by means of finely distributing nozzles. The pots were lightly sprinkler-irrigated to induce germination and growth. Transparent plastic covers were then placed on the pots until the plants had taken root. These covers ensured uniform germination of the test plants, insofar as this was not impaired by the active ingredients.

For the postemergence treatment, the test plants were either grown in the pots or transplanted to them a few days before treatment. Depending on the growth form, the plants were grown to a height of from 3 to 15 cm before being treated with the active ingredients, suspended or emulsified in water.

The plants were kept at temperatures of 10°–25° C. or 20°–35° C. as appropriate to the particular species. The experiments were run for from 2 to 4 weeks. During this period, the plants were tended and their reactions to the various treatments assessed. They were assessed on a scale of from 0 to 100, 100 denoting nonemergence of the plants or complete destruction of at least the parts above ground, and 0 denoting no damage or normal growth.

The plants used in the greenhouse experiments were made up of the following species:

| Abbreviation | Latin name | Common name |
|---|---|---|
| ECHCG | Echinochloa crus-galli | barnyardgrass |
| BROSS | Bromus spp. | brome species |
| SETIT | Setaria italica | foxtail millet |

Examples 3.6 and 3.7, applied postemergence at a rate of 3 kg of active ingredient per hectare, provided excellent control of undesirable plants.

The growth-regulating action of the compounds of the general formula I was demonstrated by the following experiments:

The active ingredients were formulated either a) as a 0.1% strength by weight solution in acetone, or b) as a 10 % strength by weight emulsion in a mixture of 70 % by weight of cyclohexanol, 20 % by weight of Nekanil® LN (Lutensol® AP6, a wetting agent with an emulsifying and dispersing action based on ethoxylated alkylphenols) and 10 % by weight of Emulphor® EL (Emulan® EL, an emulsifier based on ethoxylated fatty alcohols) and diluted to the desired concentration with acetone in the case of a) and with water in the case of b).

At the end of the experiment, the growth height of the treated plants was measured and compared with that of untreated plants. The comparative substance used for assessing the growth-regulating action was N-(2-chloroethyl)-N,N,N-trimethylamonium [sic] chloride (comparative compound A).

The following tables show by way of example the stem shortening of rape, barley and wheat plants treated with cyclohexenone derivatives 1.1 to 1.6 and 2.1, 2.3, 2.5 to 2.8:

| | | Test plants and relative growth height[*] | | |
|---|---|---|---|---|
| Comp. No. | Appl. rate [kg/ha] | Winter rape "Labrador" variety | Spring barley "Alexis" variety | Spring wheat "Star" variety |
| 1.1 | 0.75 | 74 | 74 | 92 |
| 1.2 | 0.75 | 87 | 74 | 92 |
| A | 0.75 | 94 | 106 | 92 |
| 1.1 | 0.38 | 74 | 88 | |
| 1.2 | 0.38 | 94 | 92 | 98 |
| A | 0.38 | 101 | 106 | 92 |
| CCC | 3 | 75 | 92 | 97 |
| 1.3 | 1.5 | 75 | 68 | 86 |
| 1.4 | 1.5 | 69 | 82 | 93 |
| 1.5 | 1.5 | 56 | 71 | 86 |
| 1.6 | 1.5 | 69 | 78 | 90 |
| 2.1 | 1.5 | 75 | 78 | 97 |
| 2.3 | 1.5 | 81 | 82 | 97 |
| 2.5 | 1.5 | 88 | 75 | 86 |
| 2.6 | 1.5 | 88 | 68 | 86 |
| 2.7 | 1.5 | 81 | 92 | 93 |
| 2.8 | 1.5 | 81 | 92 | 100 |

[*]100 = no effect

We claim:

1. Cyclohexenone derivatives of the formula I

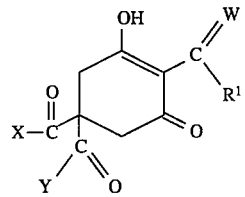

where the variables have the following meanings:

$R^1$ a $C_1$–$C_{20}$-alkyl group, a $C_2$–$C_{20}$-alkenyl group, a $C_2$–$C_{20}$-alkynyl group, a $C_3$–$C_6$-cycloalkyl group, a $C_1$–$C_4$-alkoxy-$C_1$–$C_4$-alkyl group, a $C_1$–$C_4$-alkylthio-$C_1$–$C_4$-alkyl group, the phenyl or benzyl group or a 5- or 6-membered hetaryl group having one or two heteroatoms selected from the group consisting of nitrogen, oxygen and sulfur, where the aromatic and heteroaromatic rings may furthermore carry from one to three radicals selected from the group consisting of nitro, cyano, halogen, $C_1$–$C_4$-alkyl, $C_1$–$C_4$-haloalkyl, $C_1$–$C_4$-alkoxy, $C_1$–$C_4$-alkylsulfinyl and $C_1$–$C_4$-alkylsulfonyl;

W oxygen, =—$OR^2$ or =N—$R^3$, where $R^2$ is a $C_1$–$C_6$-alkyl, $C_3$–$C_6$-alkenyl or $C_3$–$C_6$-alkynyl radical, where these radicals may furthermore carry from one to three substituents selected from the group consisting of halogen, $C_1$–$C_4$-alkyl, $C_1$–$C_4$-alkoxy, phenyl and 5- or 6-membered hetaryl having one or two heteroatoms selected from the group consisting of nitrogen, oxygen and sulfur, and the phenyl and hetaryl substituents in turn may furthermore carry from one to three radicals selected from the group consisting of nitro, halogen, $C_1$–$C_4$-alkyl, $C_1$–$C_4$-haloalkyl, $C_1$–$C_4$-alkoxy and $C_1$–$C_4$-haloalkoxy;

a 3- to 6-membered alkyl chain or a 4- to 6-membered alkenyl or alkynyl chain, where one chain member in each case is replaced with oxygen, sulfur or —SO—, —$SO_2$— or —N($R^8$)— and the chain may furthermore additionally carry from one to three substituents selected from the group consisting of halogen, $C_1$–$C_4$-alkyl, $C_1$–$C_4$-alkoxy, phenyl and 5- or 6-membered hetaryl having one or two heteroatoms selected from the group consisting of nitrogen, oxygen and sulfur, and the phenyl and hetaryl substituents may in turn furthermore carry from one to three radicals selected from the group consisting of nitro, halogen, $C_1$–$C_4$-alkyl, $C_1$–$C_4$-haloalkyl, $C_1$–$C_4$-alkoxy and $C_1C_4$-haloalkoxy, where $R^8$ is hydrogen, $C_1$–$C_6$-alkyl, $C_3$–$C_6$-alkenyl, $C_3$–$C_6$-alkynyl, $C_1$–$C_6$-alkylcarbonyl or benzoyl;

$R^3$ hydrogen, a $C_1$–$C_6$-alkyl radical, a hydroxy-$C_1$–$C_4$-alkyl, $C_1$–$C_4$-alkoxy-$C_1$–$C_4$-alkyl or $C_1$–$C_4$-alkylthio-$C_1$–$C_4$-alkyl radical, the phenyl or benzyl radical, where the aromatic rings may furthermore carry from one to three substituents selected from the group consisting of nitro, halogen, $C_1$–$C_4$-alkyl, $C_1$–$C_4$-haloalkyl and $C_1$–$C_4$-alkoxy;

X, Y a group —$OR^4$ or —$NR^5R^6$, where $R^4$ is hydrogen, a $C_1$–$C_6$-alkyl, $C_3$–$C_6$-alkenyl, $C_3$–$C_6$-alkynyl, $C_1$–$C_4$-alkoxy-$C_1$–$C_4$-alkyl or $C_1$–$C_4$-alkylthio-$C_1$–$C_4$-alkyl radical, $R^5$ is hydrogen, a $C_1$–$C_6$-alkyl, $C_3$–$C_6$-alkenyl, $C_3$–$C_6$-alkynyl, hydroxy-$C_1$–$C_4$-alkyl, $C_1$–$C_4$-alkoxy-$C_1$–$C_4$-alkyl or $C_1$–$C_4$-alkylthio-$C_1$–$C_4$-alkyl radical and $R^6$ is hydrogen, a $C_1$–$C_6$-alkyl, $C_3$–$C_6$-alkenyl, $C_3$–$C_6$-alkynyl, hydroxy-$C_1$–$C_4$-alkyl, $C_1$–$C_4$-alkoxy-$C_1$- or $C_2$-alkyl, $C_1$–$C_4$-alkylthio-$C_1$- or $C_2$-alkyl or $C_1$–$C_6$-alkylcarbonyl radical or the benzoyl radical which may furthermore carry from one to three substituents selected from the group consisting of nitro, cyano, halogen, $C_1$–$C_4$-alkyl, $C_1$–$C_4$-haloalkyl, $C_1$–$C_4$-alkoxy and $C_1$–$C_4$-alkylthio, or $R^5$ and $R^6$, together with the nitrogen atom to which they are bonded, may form a 5- or 6-membered heterocyclic structure which may contain an oxygen or sulfur atom or a group —$N(R^7)$— as a ring member, where $R^7$ is hydrogen, $C_1$–$C_6$-alkyl, $C_3$–$C_6$-alkenyl, $C_3$–$C_6$-alkynyl, $C_1$–$C_6$-alkylcarbonyl or benzoyl, and the agriculturally useful salts of I and the esters of I with $C_1$–$C_{10}$-carboxylic acids or inorganic acids.

2. A herbicide containing a liquid or solid carrier and at least one cyclohexenone derivative I as defined in claim 1, where W is the group =N—$OR^2$, or an agriculturally useful salt of these compounds or an ester of these compounds with $C_1$–$C_{10}$-carboxylic acids or with inorganic acids.

3. A method for controlling undesirable plant growth, wherein a herbicidally active amount of a cyclohexenone derivative of the formula I as defined in claim 1, where W is the group =N—$OR^2$, or an agriculturally useful salt of these compounds or an ester of these compounds with $C_1$–$C_{10}$-carboxylic acids or with inorganic acids, is allowed to act on plants or their habitat or on seed.

4. A plant growth regulator containing a liquid and/or solid carrier and at least one cyclohexenone derivative of the formula I as defined in claim 1, where W is oxygen, or an agriculturally useful salt of these compounds or an ester of these compounds with $C_1$–$C_{10}$-carboxylic acids or with inorganic acids.

5. A plant growth regulator containing a liquid and/or solid carrier and at least one cyclohexenone derivative of the formula I as defined in claim 1, where W is the group =N—$R^3$, or an agriculturally useful salt of these compounds or an ester of these compounds with $C_1$–$c_{10}$-carboxylic acids or with inorganic acids.

6. A method for regulating plant growth, wherein an amount, effective for regulating plant growth, of a cyclohexenone derivative of the formula I as defined in claim 1, where W is oxygen, or an agriculturally useful salt of these compounds or an ester of these compounds with $C_1$–$C_{10}$-carboxylic acids or with inorganic acids, is allowed to act on plants or their habitat or on the seed of the plants.

7. A method for regulating plant growth, wherein an amount, effective for regulating plant growth, of a cyclohexenone derivative of the formula I as defined in claim 1, where W is the group =N—$R^3$, or an agriculturally useful salt of these compounds or an ester of these compounds with $C_1$–$C_{10}$-carboxylic acids or with inorganic acids, is allowed to act on plants or their habitat or on the seed of the plants.

* * * * *

UNITED STATES PATENT AND TRADEMARK OFFICE
CERTIFICATE OF CORRECTION

PATENT NO.: 5,523,462

DATED: June 4, 1996

INVENTOR(S): KAST et al.

It is certified that error appears in the above-identified patent and that said Letters Patent is hereby corrected as shown below:

Column 22, claim 1, line 47, "=-OR$^2$" should read -- =N-OR$^2$ --.

Column 24, claim 5, line 23, "C$_1$-c$_{10}$-" should read -- C$_1$-C$_{10}$- --.

Signed and Sealed this

Third Day of September, 1996

Attest:

BRUCE LEHMAN

Attesting Officer

Commissioner of Patents and Trademarks